(12) United States Patent
Wellman (10) Patent No.: US 10,722,233 B2
(45) Date of Patent: Jul. 28, 2020

(54) STAPLING CARTRIDGE (71) Applicant: Intuitive Surgical Operations, Inc., Sunnyvale, CA (US)

(72) Inventor: Ashley Lynn Wellman, East Palo Alto, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 532 days.

(21) Appl. No.: 15/472,587

(22) Filed: Mar. 29, 2017

(65) Prior Publication Data
US 2017/0290586 A1 Oct. 12, 2017

Related U.S. Application Data (60) Provisional application No. 62/319,732, filed on Apr. 7, 2016.

(51) Int. Cl.
*A61B 17/072* (2006.01)

(52) U.S. Cl.
CPC ............... *A61B 17/07207* (2013.01); *A61B 2017/07271* (2013.01); *A61B 2017/07285* (2013.01)

(58) Field of Classification Search
CPC .... A61B 17/07207; A61B 2017/07271; A61B 2017/07278; A61B 2017/07285
USPC ...................................................... 227/180.1
See application file for complete search history.

(56) References Cited

U.S. PATENT DOCUMENTS

| | | | | |
|---|---|---|---|---|
| 5,040,715 A | * | 8/1991 | Green | A61B 17/07207 227/176.1 |
| 5,485,952 A | * | 1/1996 | Fontayne | A61B 17/07207 227/111 |
| 5,653,373 A | * | 8/1997 | Green | A61B 17/07207 227/175.1 |
| 9,332,974 B2 | * | 5/2016 | Henderson | A61B 17/00491 |
| 9,642,620 B2 | * | 5/2017 | Baxter, III | A61B 17/072 |
| 10,245,029 B2 | * | 4/2019 | Hunter | A61B 17/068 |
| 2004/0232199 A1 | * | 11/2004 | Shelton, IV | A61B 17/07207 227/175.2 |
| 2006/0016853 A1 | * | 1/2006 | Racenet | A61B 17/105 227/176.1 |
| 2007/0175950 A1 | * | 8/2007 | Shelton, IV | A61B 17/07207 227/176.1 |
| 2009/0206135 A1 | * | 8/2009 | Hall | A61B 17/07207 227/176.1 |
| 2011/0101067 A1 | * | 5/2011 | Johnson | A61B 17/07207 227/176.1 |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Stephen F. Gerrity
*Assistant Examiner* — Joshua G Kotis
(74) *Attorney, Agent, or Firm* — Kilpatrick Townsend & Stockton LLP (57) ABSTRACT

A stapling cartridge having an elongated rail that provides support to a moveable clamping element and resists pulling or spreading forces caused by compressing and cutting tissue. The elongated rail can directly connect the stapling cartridge to the lower jaw and completely carry the moveable clamping element, which can couple and decouple to an anvil of an upper jaw.

18 Claims, 6 Drawing Sheets

(56) References Cited

U.S. PATENT DOCUMENTS

| | | | | |
|---|---|---|---|---|
| 2011/0290854 A1* | 12/2011 | Timm | A61B 17/072 | 227/178.1 |
| 2013/0098968 A1* | 4/2013 | Aranyi | A61B 17/07207 | 227/177.1 |
| 2013/0105545 A1* | 5/2013 | Burbank | A61B 17/068 | 227/175.1 |
| 2014/0183244 A1* | 7/2014 | Duque | A61B 34/25 | 227/180.1 |
| 2014/0291379 A1* | 10/2014 | Schellin | A61B 17/068 | 227/176.1 |
| 2015/0201930 A1* | 7/2015 | Aranyi | A61B 17/07207 | 227/177.1 |
| 2015/0320423 A1* | 11/2015 | Aranyi | A61B 17/105 | 227/177.1 |
| 2015/0327862 A1* | 11/2015 | Kostrzewski | A61B 17/07207 | 227/178.1 |
| 2016/0324518 A1* | 11/2016 | Nicholas | A61B 17/072 | |
| 2017/0319205 A1* | 11/2017 | Beardsley | A61B 17/07207 | |
| 2018/0168623 A1* | 6/2018 | Simms | A61B 17/07207 | |
| 2019/0192159 A1* | 6/2019 | Simms | A61B 34/30 | |

* cited by examiner

STAPLING CARTRIDGE

RELATED APPLICATIONS

This patent application claims priority to and the benefit of the filing date of U.S. Provisional Patent Application 62/319,732, entitled "STAPLING CARTRIDGE" filed Apr. 7, 2016, which is incorporated by reference herein in its entirety.

BACKGROUND OF THE INVENTION

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

A common form of minimally invasive surgery is endoscopy, and a common form of endoscopy is laparoscopy, which is minimally invasive inspection and/or surgery inside the abdominal cavity. Reloadable stapling devices can be used in conjunction with these surgeries. The jaws of such stapling devices can include mechanisms for carrying and operating cutting devices that are separate from removable stapling cartridges. Repeated use however, can impede operation of such mechanisms due to wear, malfunctions, and tissue and staple intrusion.

BRIEF SUMMARY OF THE INVENTION

Some embodiments of the invention are related to stapling system having an elongated arm portion. A 2-axis joint can be coupled to the elongated arm portion. An end effector can be coupled to the 2-axis joint. The end effector can include an upper jaw and a lower jaw.

Some embodiments of the invention are related to a stapling cartridge. The cartridge can include a cartridge body that can be elongated from a proximal end to a distal end. The cartridge body can be contained within a lower jaw of an end effector. The cartridge body can include a plurality of openings. A plurality of staples can be held within the cartridge and can be arranged to be driven out of the plurality of openings. A shuttle assembly can be held by the cartridge body and configured to be driven by the end effector. The shuttle assembly can have a drive portion arranged to drive a shuttle from the proximal end of the cartridge body to the distal end of the cartridge body. An elongated rail can be contained within the cartridge body. The elongated rail can have an elongated track. The elongated rail can have at least one feature to attach to the lower jaw of the end effector. A clamping element can be carried by the shuttle to travel along the elongated track of the elongated rail. The clamping element can have a first retaining feature configured to moveably restrain against the elongated rail and a second retaining feature configured to moveably constrain an upper jaw of the end effector.

In some embodiments, the cartridge body can be constructed from a polymer material and the elongated rail can be constructed from a metal material.

In some embodiments, the cartridge body can be overmolded onto the elongated rail.

In some embodiments, the shuttle assembly can include a lead screw encased within the elongated rail.

In some embodiments, the shuttle assembly can include a lead screw for moving the shuttle. The lead screw can be coupled to a coupling block at the distal end of the cartridge body.

In some embodiments, the coupling block can be moveable by the lead screw to lock and unlock to the lower jaw.

In some embodiments, the clamping element can include a holding portion moveably connected to the shuttle.

In some embodiments, the clamping element can include a cutting portion arranged to travel within the elongated track of the elongated rail.

In some embodiments, the clamping element can include an anvil gliding portion adapted to engage and disengage the upper jaw at the proximal end of the cartridge body.

In some embodiments, the cartridge body can include a coupling feature about the proximal end. The coupling feature can be configured to couple to a holding feature of the upper jaw of the end effector.

In some embodiments, the elongated rail can include a distal feature configured to hold the cartridge body to the lower jaw by coupling of the holding feature to the coupling feature.

In some embodiments, the elongated rail can include a proximal feature configured to hold the cartridge body to the lower jaw by coupling of the holding feature to the coupling feature.

In some embodiments, the elongated rail can have a boxed structure.

In some embodiments, the boxed structure can be formed from sheet metal.

DETAILED DESCRIPTION OF THE INVENTION

Figure 1:
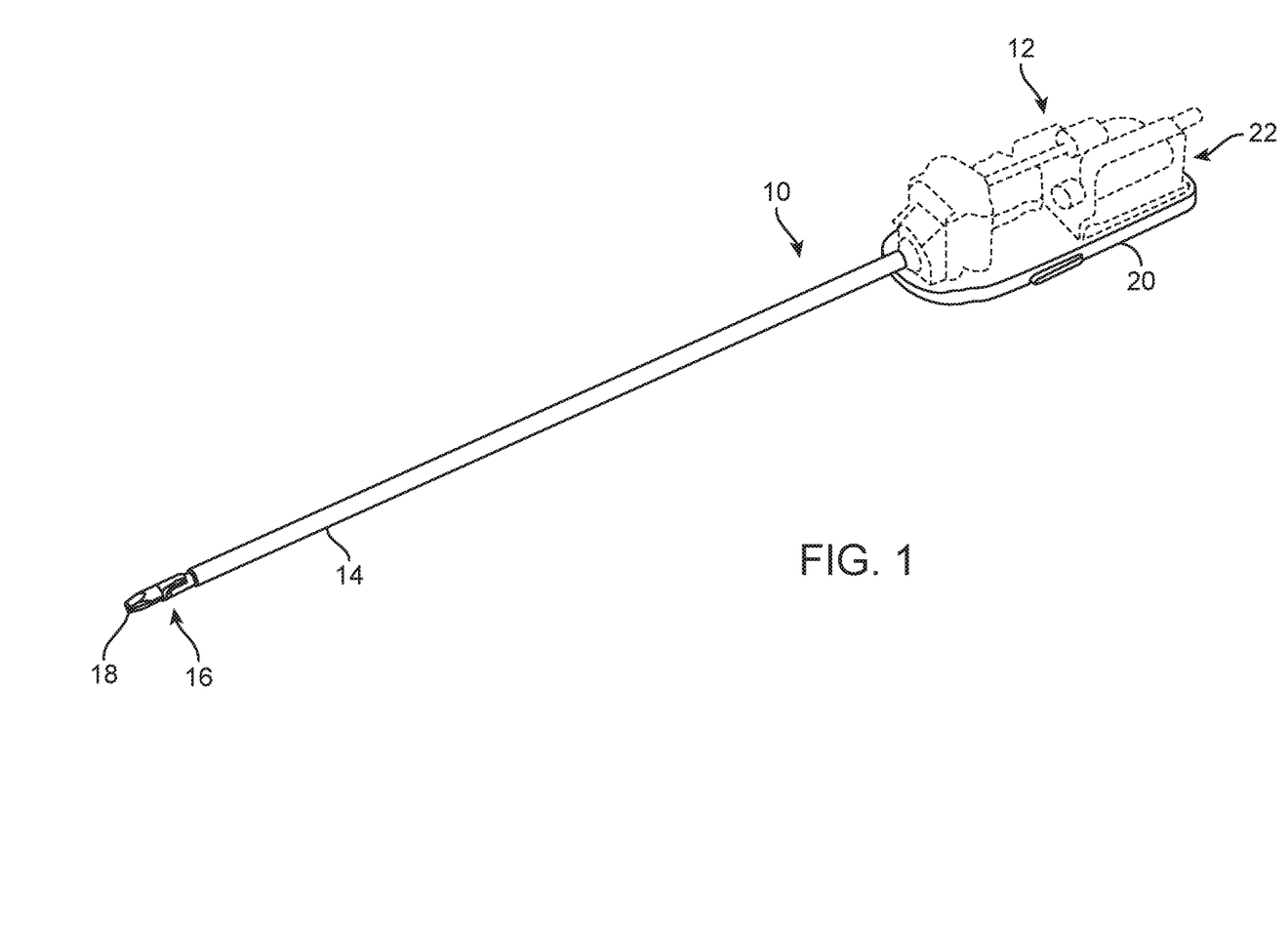
FIG. 1 is a perspective view of a surgical tool, according to some embodiments of the invention.

FIG. 1 shows a surgical tool 10 that includes a proximal chassis 12, an instrument shaft 14, and a distal end effector 16 having a jaw 18 that can be articulated to grip a patient tissue. The proximal chassis 20 includes input couplers 22 that may interface with and be driven by corresponding output couplers of a telesurgical surgery system, such as the system disclosed within Pub. No. US20140183244A1, which is incorporated by reference herein. The input couplers 22 are drivingly coupled with drive shafts that are disposed within the instrument shaft 14. The drive shafts are drivingly coupled with the end effector 16.

Figure 2:
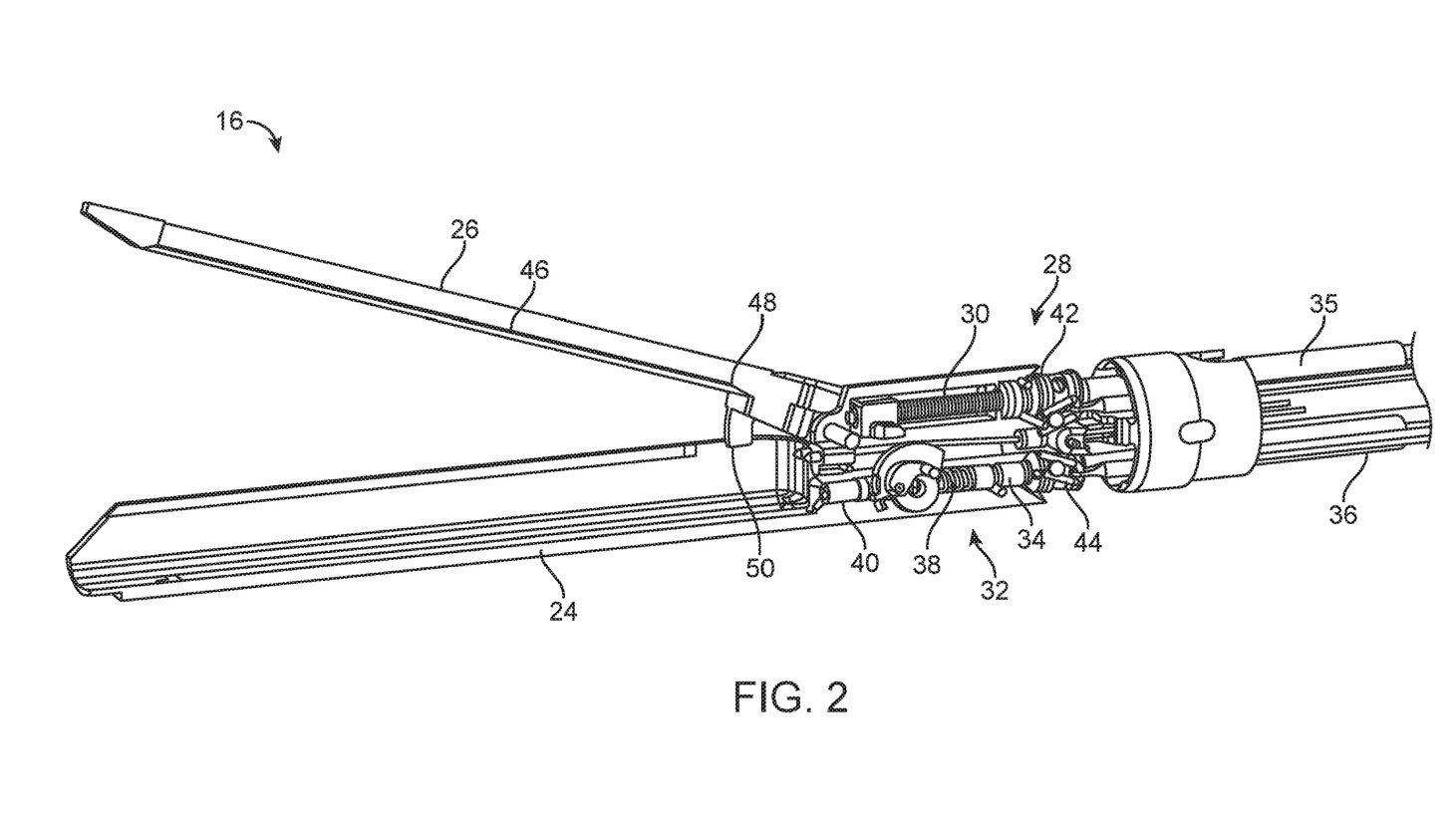
FIG. 2 is a cross-sectional view of an end effector, according to some embodiments of the invention.

FIG. 2 is a cross-sectional view showing details of end effector 16 that includes a lower jaw 24, an upper jaw 26, a two degree of freedom wrist 28, a rotationally-driven clamping mechanism 30, and a spring loaded coupling 32. The lower jaw 24 is configured to accommodate and support a stapling cartridge, as well as position the cartridge relative to the spring loaded coupling 32. The upper jaw 26 is pivotally coupled with the lower jaw 24 to articulate relative to the lower jaw 24 to clamp tissue.

The two degree of freedom wrist 28 provides for attachment of the end effector 16 to the elongated instrument shaft 14 for articulation of the end effector 16 about two orthogonal axes relative to the instrument shaft 14. The rotationally-driven clamping mechanism 30 actuates the upper jaw 26 relative to the lower jaw 24 to securely clamp tissue between the upper and lower jaws. The clamping mechanism 30 is rotationally driven by a first drive shaft 35 disposed internal to the instrument shaft 14.

The spring-loaded coupling 32 rotationally couples a lead screw of the cartridge with an extension shaft 34, which is driven by a second drive shaft 36 disposed internal to the instrument shaft 14. The spring-loaded coupling 32 includes a coil spring 38 and a coupling fitting 40. In the embodiment shown, the coupling fitting 40 employs a three-lobe spline receptacle that interfaces with three-sided external surfaces of a rotational input (e.g. rotational input 129 of the lead screw 128 of FIG. 3) and of the extension shaft 34. The coupling fitting 40 accommodates angular misalignment of the three-lobe spline that might occur when a cartridge is installed into end effector 16. The coupling fitting 40 fully engages the three-lobe spline when rotated into angular alignment. Rotation of a lead screw can be used to translate a drive member of the cartridge. The resulting motion of the drive member can be used to distally advance a shuttle and a clamping element (including an integrated or non-integrated knife element) to deploy the staples and to cut the clamped tissue down the center of the rows of deployed staples.

The end effector 16 includes a first universal joint assembly 42 and a second universal joint assembly 44. The first universal joint assembly 42 rotationally couples the clamping mechanism 30 to the first drive shaft 35. The second universal joint assembly 44 rotationally couples the extension shaft 34 to the second drive shaft 36. Each of the first and second universal joint assemblies 42, 44 is configured to transmit torque through a range of angles suitable to the range of pitch and yaw of the end effector 16 relative to the instrument shaft 14. The first and second drive shafts 35, 36 are disposed offset to the centerline of the instrument shaft 14, which may be independently rotated.

The upper jaw 26 includes an elongated anvil portion 46, which includes a bottom surface having staple forming recesses configured and positioned relative to the staple openings of the cartridge to form the staples into a "B" shape upon deployment of the staples. The anvil portion 46 includes an on-ramp portion 48, which has a beveled ramp to allow a clamping element of a stapling cartridge to engage and disengage the upper jaw 26 at the on-ramp portion 48. Movement of the clamping element over the upper jaw 26 serves to forcibly secure the upper jaw 26 over tissue with respect to the lower jaw 24, to allow the clamping element to cut tissue and deploy staples from the cartridge. The upper jaw 26 includes one or more holding features 50 which can be male shaped to fit within complimentary female shaped features of the cartridge, such that closing the upper jaw 26 to the lower jaw 24 causes the holding features 50 to secure the cartridge to the lower jaw 24.

Figure 3:
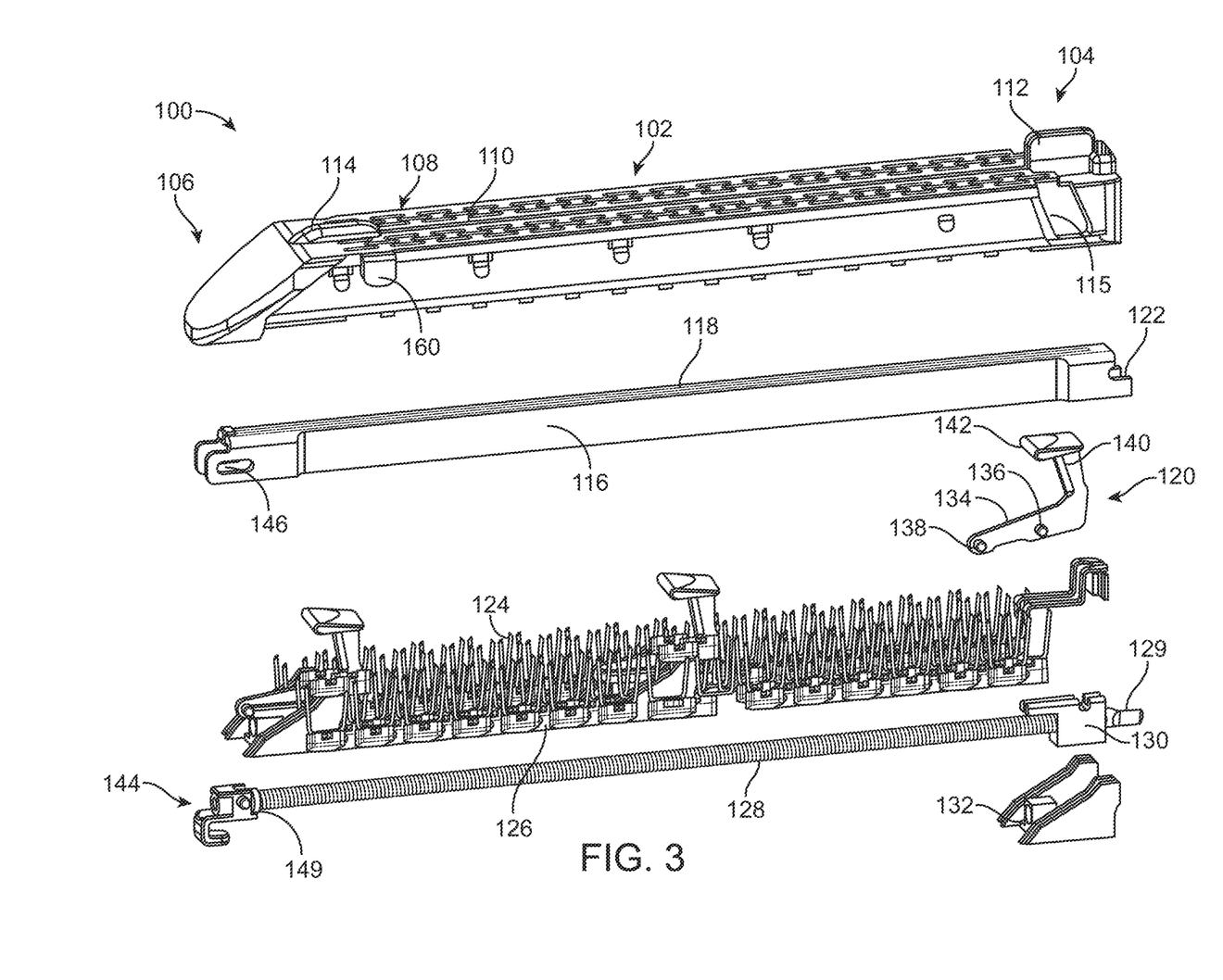
FIG. 3 is an exploded view of a stapling cartridge, according to some embodiments of the invention.

FIG. 3 shows an exploded view of a demountably attachable cartridge 100 of a linear stapling and cutting surgical instrument, in accordance with many embodiments. The cartridge 100 is configured to removably attach to a jaw of an end effector, such as end effector 16. The cartridge has a cartridge body 102 with proximal end 104 that is attached to the jaw of the end effector and a distal end 106 disposed at a corresponding distal end of the jaw of the end effector. The overall length of the cartridge 100 can be greater than 45 mm, for example, over 60 mm. The cartridge body 102 includes multiple rows of staple openings 108, a longitudinal slot 110, a proximal knife garage 112, and a distal knife garage 114. In some embodiments, a staple is disposed in each of the staple openings for deployment there from. The cartridge body 102 also includes receiving features 115 adapted to receive the aforementioned holding features 50 of the upper jaw 26.

An elongated rail 116 is contained within the cartridge body 102. The elongated rail is elongated between the proximal end 104 and distal end 106 of the cartridge body, and can be constructed from a material, such as metal. The cartridge body 102 can be constructed from a relatively more flexible material such as a polymer. Here, the elongated rail 116 has at least a partially boxed construction to resist pulling or spreading forces caused by compressing and cutting tissue, and can be stamped from sheet metal, such as stainless steel. The elongated rail 116 can float within the cartridge body 102, or be attached to the cartridge body 102 by way of adhesive or fasteners, or in some embodiments the cartridge body 102 is molded over the elongated rail 116.

The elongated rail 116 includes a rail slot 118 that aligns with the longitudinal slot 110 of the cartridge body 102. Both the rail slot 118 and the longitudinal slot 110 accommodate a cutting blade member 140 of a clamping element 120 extending there from as the clamping element 120 is moved from the proximal knife garage 112 to the distal knife garage 114. In operation, the staples are deployed starting at the cartridge proximal end 104 and proceeding to the cartridge distal end 106. The cutting blade member 140 is moved to trail the stapling of the tissue to ensure that only fully stapled tissue is cut.

The elongated rail 116 includes a proximal feature 122, which is shown as a keyed contour of the elongated rail 116 configured to mate with a complimentary contour of the lower jaw. The illustrated components also include staples 124, staple pushers 126, lead screw 128, drive member 130, and a shuttle 132. Rotational input 129 of the lead screw 128 can couple to the coupling fitting 40 shown at FIG. 2. The staple pushers 126 interface with the staples 124 and slidingly interface with the cartridge body 102. As shown, motion of the drive member 130 and shuttle 132 along the lead screw 128 results in engagement of the staple pushers 126 by ramp surfaces of the shuttle 132 to drive the staple pushers 126 up relative to the cartridge body 102 to deploy the staples 126 as the shuttle 132 moves towards the distal end 106. Multiple clamping elements and shuttles are shown here, and at other figures, to better illustrate operation of the cartridge 100, however, generally only one clamping element 120 and shuttle 132 are used.

The clamping element 120 includes a carrying portion 134 having proximal protrusions 136 and distal protrusions 138 that movingly interface with the drive member 130, which can drive shuttle 132. In other embodiments, the drive member 130 and shuttle 132 can be integrated into a single shuttle assembly. Operational details of this interface are found in the aforementioned Pub. No. US20140183244A. Blade member 140 extends from the carrying portion 134 to a gliding portion 142. The gliding portion 142 is configured to ride over the upper jaw 26 and constrain the upper jaw 26 to the lower jaw 24 as the clamping element 120 moves from the proximal end 104 to the distal end 106 of the cartridge body 102. In a similar manner, the proximal protrusions 136 and/or distal protrusion 138 of the clamping element 120 glide and constrain against the elongated rail 116 to constrain the lower jaw 24 to the upper jaw 26 as the clamping element 120 moves from the proximal end 104 to the distal end 106 of the cartridge body 102.

A coupling block 144 is located at the distal end 106 of the cartridge body 102. The coupling block 144 is moveable within slot 146 of the elongated rail 116 and is adapted to lock and unlock to the lower jaw 24 by movement of the lead screw 128, which is discussed in further detail below.

Figure 4A:
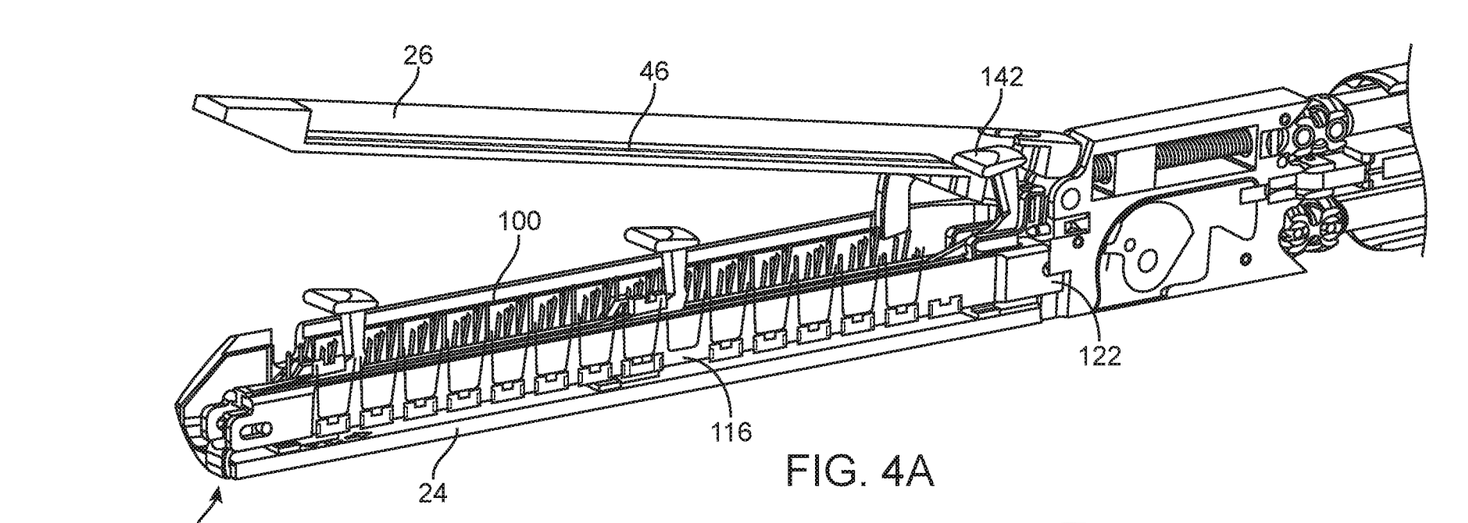
FIGS. 4A-4C are cross-sectional views of a stapling system, according to some embodiments of the invention.
Figure 4B:
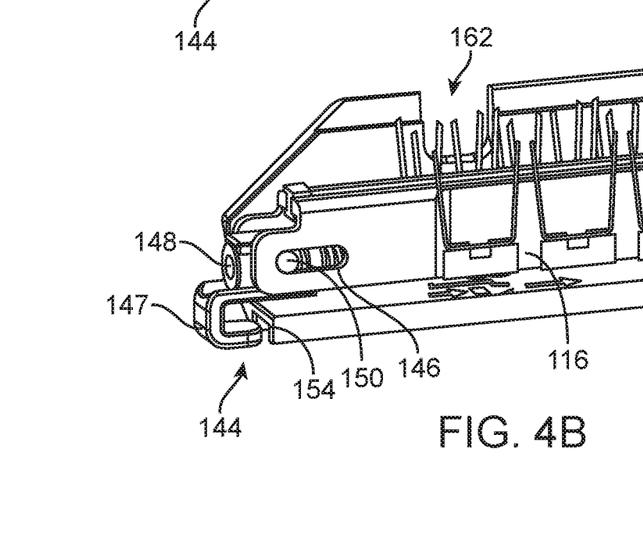
Figure 4C:
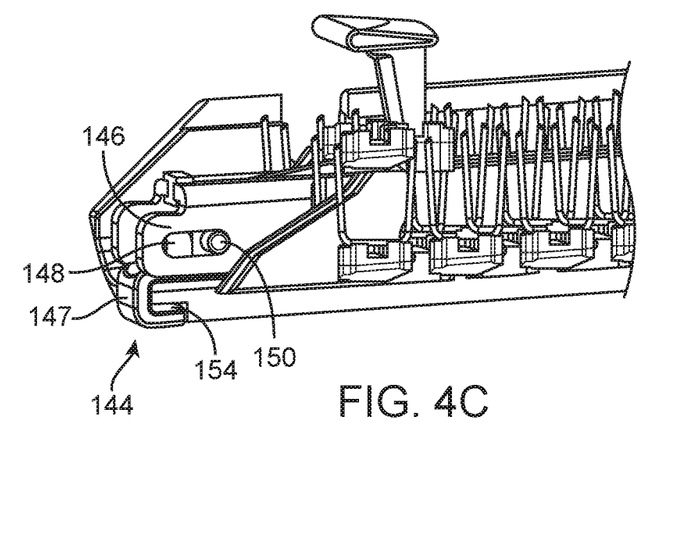

FIGS. 4A-4C show the cartridge 100 coupled to the lower jaw 24 of the end effector 16. The cartridge body 102 is not shown in this view to better illustrate how the cartridge 100 can in some embodiments be secured to the lower jaw 24. The coupling block 144 includes a movable latch member 147 retained by a latch retaining nut 148. The latch member 147 can have a bore that allows rotation of the lead screw 128, and can be captured axially between a shoulder 149 on the lead screw 128 and a retaining element, such as laser-welding the latch retaining nut 148 in place. The latch member 147 includes a captured or integrated protrusion 150 (also called "pin 150" when in the shape of a pin) that is arranged to slide within a slot 146 located at the distal end of the elongated rail 116. The latch retaining nut 148 includes internal threads mated to lead screw 128. Actuation of the lead screw 128 with latch retaining nut 148 causes the latch member 147 to move distally from an unsecured position shown at FIG. 4B and secure to a distal slot 154 of the lower jaw 24 shown at FIG. 4C, as limited by the protrusion 150 within the slot 146 or by the latch member 147 hard-stopping against the lower jaw 24. Thus, the elongated rail 116 becomes secured to the lower jaw 24.

In use, the upper jaw 26 and lower jaw 24 can be positioned to cut and staple tissue. The cartridge 100 is first secured to the lower jaw 24 by sliding movement of the cartridge onto the lower jaw 24 such that the proximal feature 122 of the elongated rail 116 fits into a complimentary shaped portion of the lower jaw 24. The coupling block 144 is also actuated to secure the distal end of the elongated rail 116 to the distal end of the lower jaw 24. In addition, downward movement of the upper jaw 26 causes holding features 50 of the upper jaw 26 to secure to the receiving features 115 of the cartridge body 102 to further secure the cartridge 100 from distal ejection. However, inclusion of the holding features 50 is optional due to the securement provided by the coupling block 144. Instead of, or in addition to, the use of the holding features 50, cartridge keying features 160 in cartridge body 102 (shown at FIG. 3) may be used to secure to the receiving features 162 in lower jaw 24 to secure the cartridge 100 from distal ejection.

The upper jaw 26 is forcibly clamped to the lower jaw 24 by movement of the gliding portion 142 over the upper jaw 26. This can cause the lower jaw 24 and upper jaw 26 to deform from compression of tissue located distally of the clamping element 120. The clamping element 120 helps prevent excessive flexure of the lower jaw 24 and upper jaw 26 by mitigating bending and torsion of the lower jaw 24 and upper jaw 26. This can be very advantageous for cartridges greater than 45 mm for example or for cartridges of smaller material cross-sections, which can encounter excessive clamping flexure due to length.

Figure 5:
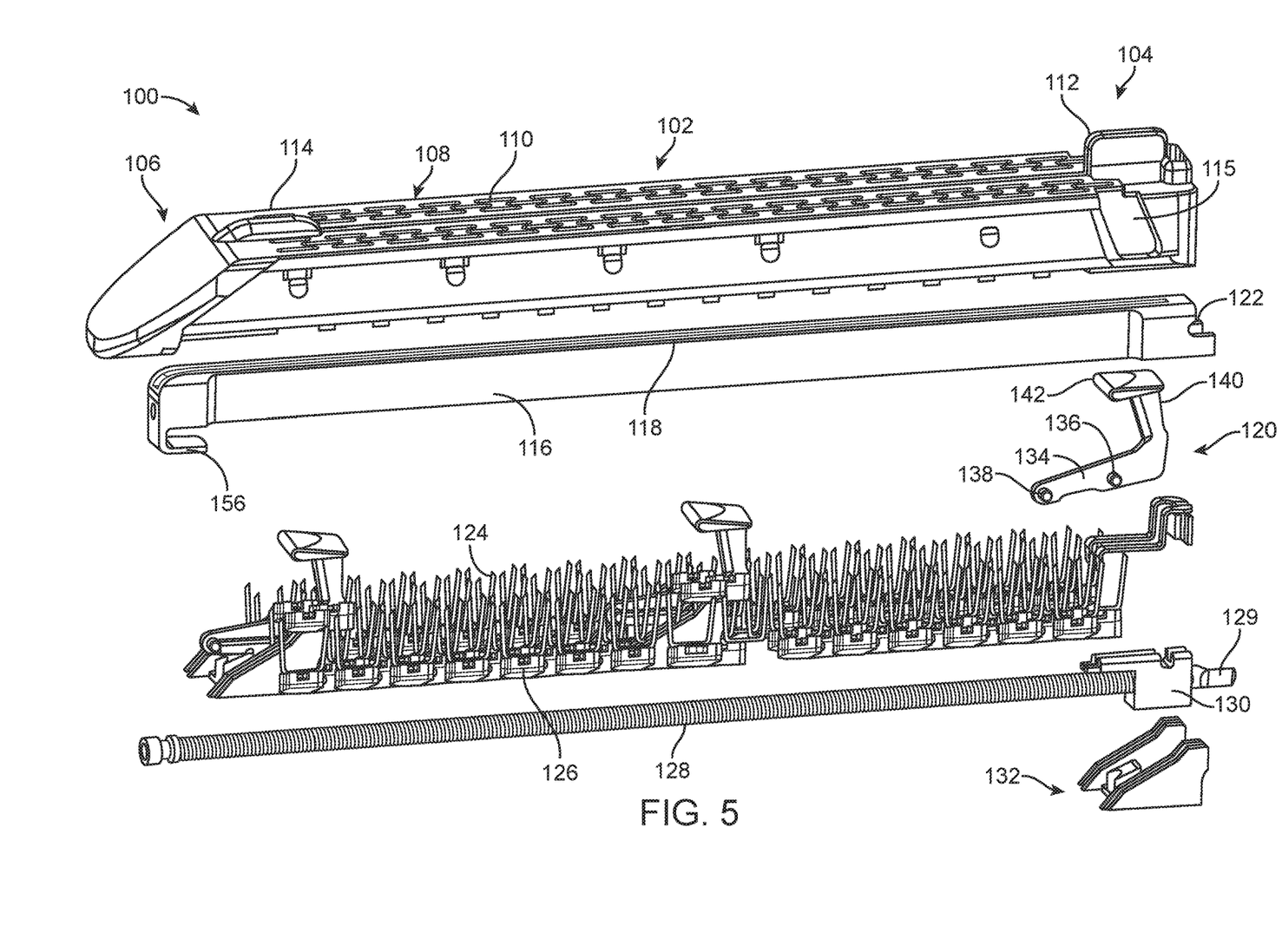
FIG. 5 is an exploded view of a stapling cartridge, according to some embodiments of the invention.
Figure 6A:
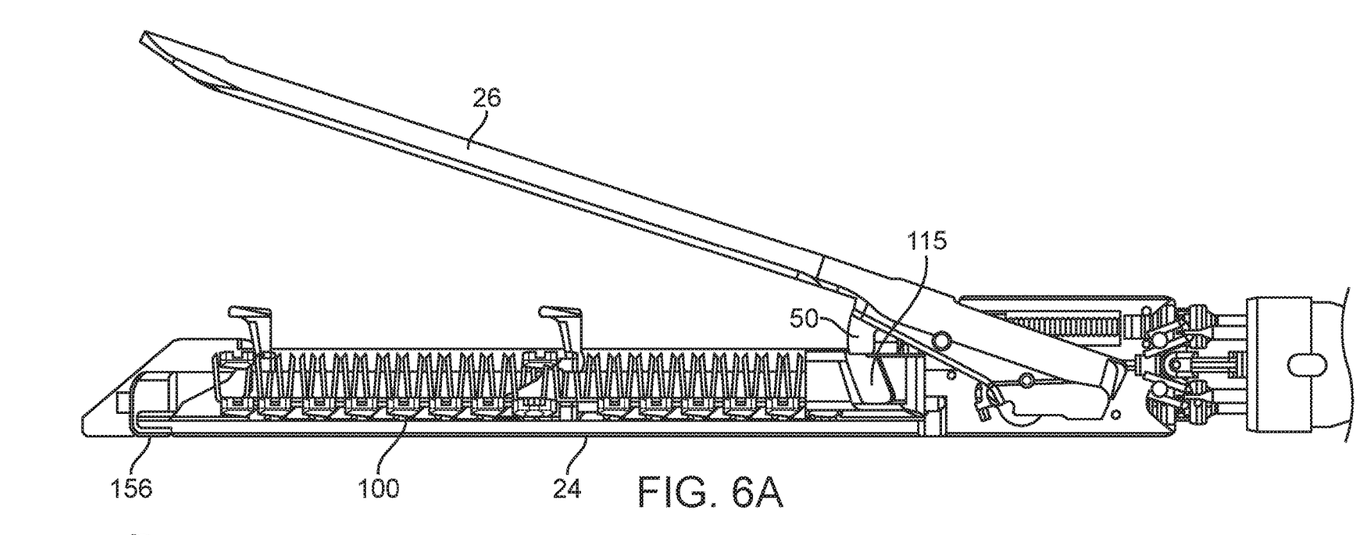
FIGS. 6A and 6B are cross-sectional views of a stapling system, according to some embodiments of the invention.
Figure 6B:
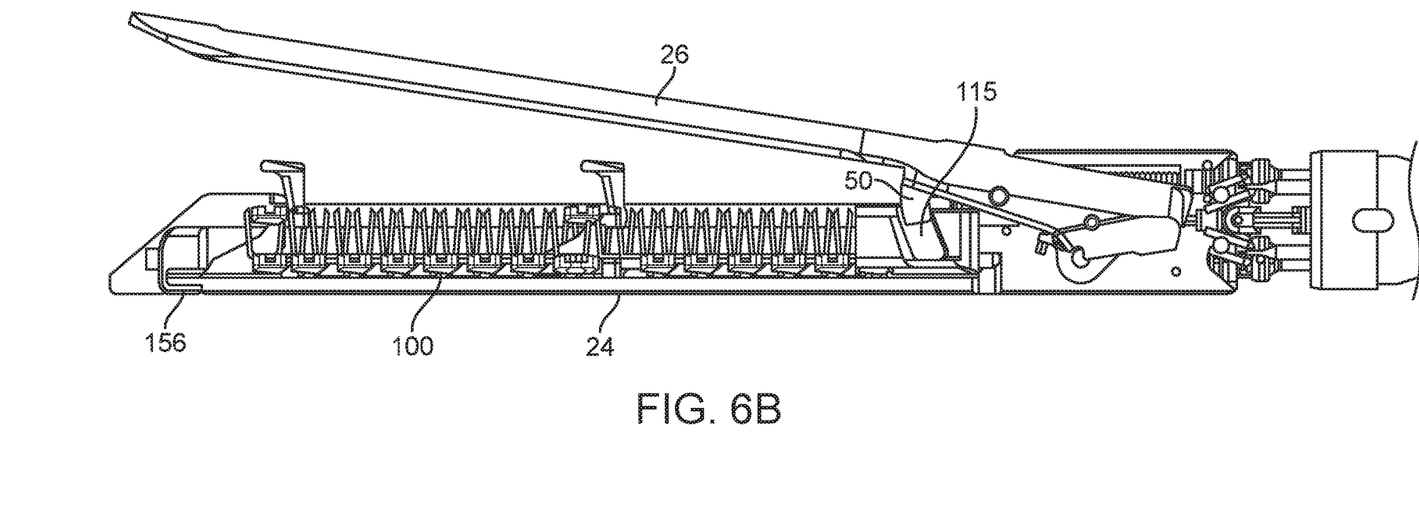

FIG. 5 shows an alternative construction of the cartridge 100, which shares almost the same construction shown at FIG. 3. Hence, shared features will not be repeated here for the sake of brevity. However, here the elongated rail 116 does not include the coupling block 144. Instead, the elongated rail 116 includes a distal tab 156 that is configured to couple with the distal slot 154 of the lower jaw 24. As shown at FIGS. 6A and 6B, the cartridge 100 is first secured to the lower jaw 24 by sliding movement of the cartridge onto the lower jaw 24 such that the proximal feature 122 of the distal tab fits into a complimentary shaped portion of the lower jaw 24. In addition, downward movement of the upper jaw 26 as shown at FIG. 6B causes holding features 50 of the upper jaw 26 to secure to the receiving features 115 of the cartridge body 102 to further secure the cartridge 100 from distal ejection. When in use, motion of the upper jaw 26 can be limited such that the holding features 50 and receiving features 115 remain engaged, as shown at FIG. 6B. In this manner, the cartridge 100 is secured to the end effector 16 for use.

Other variations are within the spirit of the present invention. The various aspects, embodiments, implementations or features of the described embodiments can be used separately or in any combination. Various aspects of the described embodiments associated with operation of tele-surgical tools can be implemented by software, hardware or a combination of hardware and software. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A stapling cartridge comprising:
 a cartridge body elongated from a proximal end to a distal end, wherein the cartridge body is configured to be removably attached to a lower jaw of an end effector, and wherein the cartridge body defines openings;
 staples held within the cartridge body and arranged to be driven out of the openings;
 a shuttle assembly held by the cartridge body and configured to be driven by the end effector, wherein the shuttle assembly comprises a shuttle that is configured to be driven from the proximal end of the cartridge body to the distal end of the cartridge body to drive the staples out of the openings, and wherein the shuttle assembly comprises a lead screw for moving the shuttle;
 an elongated rail contained within the cartridge body, the elongated rail having an elongated rail slot, the elongated rail having at least one feature configured to be removably attached to the lower jaw of the end effector;
 a clamping element carried by the shuttle assembly to travel along the elongated rail slot of the elongated rail, the clamping element comprising a carrying portion, a gliding portion, and a cutting blade member that extends from the carrying portion to the gliding portion and through the elongated rail slot, the carrying portion being interfaced with the shuttle assembly so as to be carried by the shuttle assembly, the carrying portion slidingly interfacing with the elongated rail, wherein the gliding portion is adapted to slidingly interface with an upper jaw of the end effector;
 a latch member having a bore that accommodates a portion of the lead screw and rotation of the lead screw; and
 a latch retaining nut having internal threads mated to the lead screw configured for selective translation of the latch retaining nut relative to the lead screw for selective engagement of the latch member with the lower jaw, and wherein the latch member is captured axially between a shoulder of the lead screw and the latch retaining nut.

2. The stapling cartridge of claim 1, wherein the cartridge body comprises a polymer material and the elongated rail comprises a metal material.

3. The stapling cartridge of claim 2, wherein the cartridge body is overmolded onto the elongated rail.

4. The stapling cartridge of claim 1, wherein:
 the shuttle assembly comprises the lead screw encased within the elongated rail; and
 the carrying portion is disposed between the lead screw and the elongated rail slot.

5. The stapling cartridge of claim 1, wherein:
 the gliding portion is configured to slidingly interface with an elongated anvil portion of the upper jaw; and
 the gliding portion is adapted to engage and disengage a proximal end portion of the elongated anvil portion.

6. The stapling cartridge of claim 1, wherein:
 the cartridge body comprises a receiving feature configured to interface with the upper jaw to secure the cartridge body to the lower jaw against distal ejection of the cartridge body from the lower jaw.

7. The stapling cartridge of claim 6, wherein the at least one feature comprises a distal feature configured to be interfaced with the lower jaw to hold the cartridge body to the lower jaw.

8. The stapling cartridge of claim 7, wherein the at least one feature comprises a proximal feature configured to be interfaced with the lower jaw to hold the cartridge body to the lower jaw.

9. The stapling cartridge of claim 1, wherein the elongated rail comprises a boxed structure.

10. The stapling cartridge of claim 1, wherein:
 the shuttle assembly comprises a drive member that drives the shuttle from the proximal end of the cartridge body to the distal end of the cartridge body;
 the carrying portion comprises proximal protrusions and distal protrusions that movingly interface with the drive member; and
 the proximal protrusions and the distal protrusions slidingly interface with the elongated rail.

11. The stapling cartridge of claim 10, wherein the drive member and the shuttle are integrated into a single shuttle assembly.

12. A stapling system comprising:
 an instrument shaft;
 a two degree of freedom wrist coupled to the instrument shaft;
 an end effector coupled to the two degree of freedom wrist, the end effector comprising an upper jaw and a lower jaw, wherein the upper jaw comprises a holding feature;
 a stapler cartridge removably mountable to the lower jaw, the stapler cartridge comprising:
  a cartridge body elongated from a proximal end to a distal end, the cartridge body configured to removably couple to the lower jaw, wherein the cartridge body defines openings, and wherein the cartridge body comprises a receiving feature configured to receive the holding feature during closing of the upper jaw to the lower jaw to secure the cartridge body to the lower jaw against distal ejection of the cartridge body from the lower jaw;
  staples held within the cartridge body and arranged to be driven out of the openings;
  a shuttle assembly held by the cartridge body and configured to be driven by the end effector, the shuttle assembly comprising a shuttle that is driven from the proximal end of the cartridge body to the distal end of the cartridge body to drive the staples out of the openings;
  an elongated rail held by the cartridge body, the elongated rail having an elongated rail slot, wherein the elongated rail has at least one feature to removably attach to the lower jaw, and wherein the at least one feature comprises a distal feature configured to be interfaced with a distal end portion of the lower jaw to hold the cartridge body to the lower jaw; and
  a clamping element carried by the shuttle assembly to travel along the elongated rail slot of the elongated rail, the clamping element comprising a carrying portion, a gliding portion and a cutting blade member that extends from the carrying portion to the gliding portion and through the elongated rail slot, the carrying portion being interfaced with the shuttle assembly so as to be carried by the shuttle assembly, the carrying portion slidingly interfacing with the elongated rail, the gliding portion slidingly interfacing with the upper jaw.

13. The stapling system of claim 12, wherein the cartridge body comprises a polymer material and the elongated rail comprises a metal material.

14. The stapling system of claim 12, wherein:
the shuttle assembly comprises a lead screw encased within the elongated rail; and
the carrying portion is disposed between the lead screw and the elongated rail slot.

15. The stapling system of claim 12, further comprising a movable latch member and a latch retaining nut, wherein:
the shuttle assembly comprises a lead screw for moving the shuttle;
the movable latch member has a bore that accommodates a portion of the lead screw and rotation of the lead screw;
the movable latch member is captured axially between a shoulder of the lead screw and the latch retaining nut; and
the latch retaining nut includes internal threads mated to the lead screw configured for selective translation of the latch retaining nut relative to the lead screw for selective engagement of the movable latch member with the lower jaw.

16. The stapling system of claim 12, wherein the elongated rail comprises a boxed structure.

17. The stapling system of claim 12, wherein:
the shuttle assembly comprises a drive member that drives the shuttle from the proximal end of the cartridge body to the distal end of the cartridge body;
the carrying portion comprises proximal protrusions and distal protrusions that movingly interface with the drive member; and
the proximal protrusions and the distal protrusions slidingly interface with the elongated rail.

18. The stapling system of claim 17, wherein the drive member and the shuttle are integrated into a single shuttle assembly.

* * * * *